United States Patent [19]

Chester

[11] 4,305,392

[45] Dec. 15, 1981

[54] ENDOTRACHEAL TUBE WITH SUCTION DEVICE

[76] Inventor: Martin H. Chester, 25310 Tierra Grande, Carmel, Calif. 93923

[21] Appl. No.: 947,150

[22] Filed: Sep. 29, 1978

[51] Int. Cl.³ .............................................. A61M 1/00
[52] U.S. Cl. ................................ 128/276; 128/207.15
[58] Field of Search ....................... 128/276, 341–344, 128/347–349 B, 350 R, 351, 207.14, 207.15, 207.16, 207.17, 207.18, 768, 246

[56] References Cited

U.S. PATENT DOCUMENTS

| | | | |
|---|---|---|---|
| 2,470,665 | 5/1949 | Stiehl | 128/348 |
| 3,173,418 | 3/1965 | Baran | 128/351 |
| 3,421,510 | 1/1969 | Kettenbach | 128/350 R |
| 4,036,210 | 7/1977 | Campbell | 128/351 |

Primary Examiner—C. Fred Rosenbaum
Attorney, Agent, or Firm—Sughrue, Mion, Zinn, Macpeak and Seas

[57] ABSTRACT

An endotracheal tube of the inflatable cuff type and having a suction chamber adjacent the upper side of the cuff. The suction chamber is in the shape of a bulge having four ports equally spaced about the periphery of the bulge and facing upwardly. Suction applied to the chamber will extract fluids from the trachea above the cuff without invaginating the tracheal mucosa. Medicinal fluids may also be introduced into the trachea via the suction chamber and ports.

8 Claims, 4 Drawing Figures

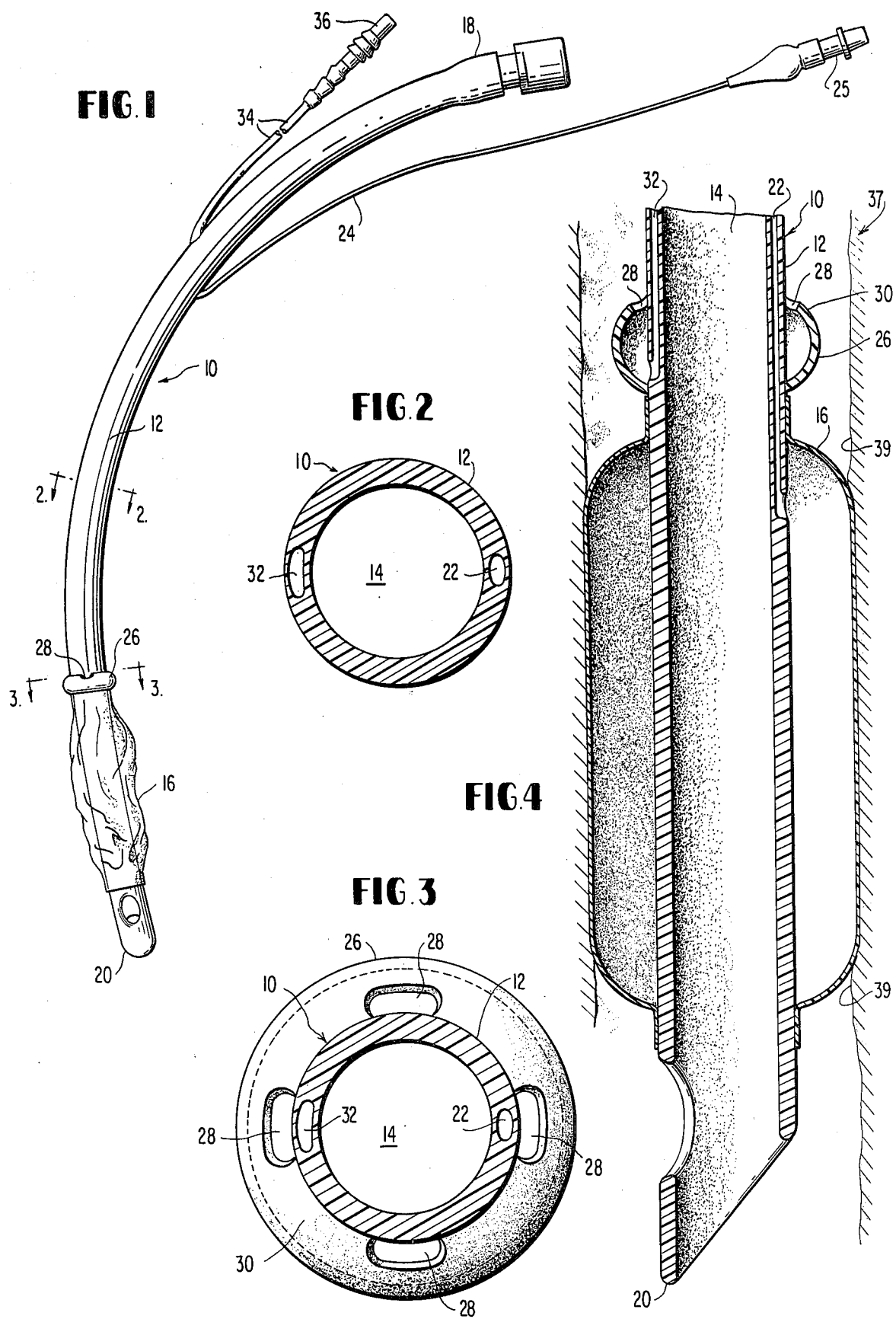

ENDOTRACHEAL TUBE WITH SUCTION DEVICE

BACKGROUND OF THE INVENTION

1. Field of the Invention

The invention relates generally to the field of endotracheal tubes and, more particularly, to an endotracheal tube of the inflatable cuff type.

2. Description of the Prior Art

Endotracheal tubes having inflatable cuffs and/or suction means are broadly known in the prior art. However, the suctioning means of such prior art devices are oriented such that they cause injury to the tracheal mucosa by grabbing or invaginating the tracheal mucosa when suction is applied. Examples of such prior art are U.S. Pat. Nos. 2,854,982; 3,173,418; 3,322,126; 3,788,326, and 3,889,688.

SUMMARY OF THE INVENTION

The primary object of the present invention is to provide an improved endotracheal tube having a suction device which will not cause injury to the tracheal mucosa.

A more specific object is to provide such an endotracheal tube in which the suction device is a chamber in the form of a bulge having suction ports which do not contact the tracheal wall and which face generally upwardly to prevent invagination of tracheal mucosa.

Another object of the invention is to provide an improved endotracheal tube of the inflatable cuff type in which said suction chamber is located on the upward side of the inflatable cuff and adjacent thereto to permit the introduction of medicinal fluids into the trachea in the area above and around the inflatable cuff.

BRIEF DESCRIPTION OF THE DRAWING

FIG. 1 is an elevational view of an endotracheal tube having the improved suction device.

FIG. 2 is a cross-sectional view taken along line 2—2 of FIG. 1.

FIG. 3 is a cross-sectional view taken along line 3—3 of FIG. 1.

FIG. 4 is a cross-sectional view showing the improved endotracheal tube inserted in a patient's trachea.

DETAILED DESCRIPTION OF THE PREFERRED EMBODIMENT

FIG. 1 shows the improved endotracheal tube 10 having a cylindrical wall 12 and a main lumen 14. An inflatable cuff 16 is suitably secured around the tube wall 12 at a point between the proximal end 18 and the distal end 20 of the tube 10. A lumen 22 located within the tube wall 12 extends from the cuff 16 to the proximal end of the tube 10 where it is joined to an external tube 24 having an adapter 25 to be connected to a suitable source of compressed air for inflating and expanding the high volume, low pressure cuff 16 which then engages the tracheal wall after the tube 10 is inserted into the trachea.

Located adjacent the inflatable cuff 16, and between the cuff and the proximal end 18 of the tube 10, is a suction chamber 26 having four ports 28 equally spaced about the periphery of the chamber. The chamber is in the shape of a bulge and has a diameter which is approximately one-third greater than that of the tube 10. The ports 28 are formed in the chamber surface 30 facing upwardly or toward the proximal end 18. This surface is inclined at an acute angle to the vertical axis of the endotracheal tube 10, and the four ports 28 are located immediately adjacent to the outer wall of tube 10 and spaced inwardly from the outer edge of chamber 26. Because of this structure of the suction chamber 26 and the location of the ports 28 therein, the ports do not contact the tracheal wall, and furthermore, because of the upwardly facing direction of the ports, when suction is applied to the suction chamber 26, invagination or grabbing of the tracheal mucosa will not occur.

A lumen 32, located in the tube wall 12, extends from the suction chamber 26 to the upper or proximal end 18 of tube 10 where it is connected to a catheter 34 which in turn is connected to a suitable adapter 36 for connecting the lumen to a source of suction or to a syringe. Lumen 32 is preferably ovoid in cross-section.

The endotracheal tube 10 is constructed of polyethylene or vinyl plastic. The inside diameter tube typically ranges from 3 mm to 10 mm. The outer diameter of the suction chamber 26 typically ranges from 4 to 14 mm. The material and construction of the suction chamber is of sufficient strength to resist collapse when suction or negative pressure is applied to the suction chamber.

In the preferred embodiment, there are four suction ports 28 equally spaced about the periphery of the suction chamber. It has been found that this number provides for most efficient suction without compromising the structural strength of the walls, even though the invention contemplates that more or fewer ports could be used. The ports are preferably ovoid in shape to provide maximum cross-sectional suctioning area without increasing the dimensions of the suction chamber. Furthermore, more effective suction of large blood clots and thickened secretions is obtained by this configuration. Moreover, when the suction chamber and ports are utilized to introduce anesthesia into the trachea, these suction ports function efficiently to spread the injected local anesthetic solution toward the upper end of the trachea and larynx above the inflatable cuff 16.

FIG. 4 shows the improved endotracheal tube in a patient's trachea 37 with the cuff 16 inflated to engage the inner wall 39 of the trachea. As shown, the suction chamber 26 has a diameter smaller than that of the inflated cuff 16 and does not contact the tracheal wall.

In use, the endotracheal tube 10 is inserted into the patient's trachea. Immediately following intubation, the physician may choose to inject local anesthetic solution through the suction chamber and ports. This procedure will anesthetize the trachea and minimize the hazards of intubation. These hazards include cardiac arrhythmias, such as premature ventricular beats, venticular fibrillation and cardiac arrest. Other complications of intubation, such as hypertension, bucking or paroxysms of coughing, will also be avoided.

After the cuff 16 is inflated to engage the wall of the trachea, the upper airway above the cuff may be kept free of secretions by use of the suction device, thereby avoiding the "silent" aspiration syndrome and, consequently, preventing pulmonary complications.

During the administration of an anesthetic, frequent applications of local anesthetic solution may be used to keep the upper trachea anesthetized, thereby enabling the physician to maintain an anesthetic using low concentrations of gas and intravenous anesthetic agents.

Critical patients who are intubated in the intensive care unit may be successfully managed on a mechanical ventilator without the use of narcotics or muscle relaxants. The suction device will confine the local anesthetic solution to the upper airway and cuff area so that very little dispersal of local anesthetic agent will occur. This action will minimize the danger of toxic reactions to the local anesthetic agent.

Prior to extubation, the device may be used to irrigate and suction the upper airway to remove gastric secretions, blood or pus. Post-operative pulmonary complications are thus avoided.

An important feature of the improved endotracheal tube with the novel suction chamber is that the design of the chamber, and the shape and orientation of the suction ports, is such that, when suction is applied to the suction chamber, the trachea mucosa will not be invaginated, thereby preventing injury to the trachea. By contrast, the orientation of suction ports in the prior art devices will cause grabbing or invagination of the trachea mucosa.

Even though the invention has been disclosed as an endotracheal tube, it is clear that the same structure could be used for endobronchial and tracheostomy tubes. Furthermore, the improved endotracheal tube permits local anesthesia to be inserted into the area above the inflated cuff where it is most required. In this way, local anesthesia can be used as a valuable adjunct to general anesthesia. Moreover, the cuff can be momentarily relaxed to permit the local anesthesia to bathe the tracheal area around the cuff. A jet stream of irrigation fluid may also be applied via lumen 32 to break up blood clots or thickened mucoid secretions, so that they later can be easily removed by suction applied to lumen 32.

I claim:

1. An endotracheal tube for insertion into the trachea and having a proximal and a distal end, said tube comprising:
   (a) a main lumen having a cylindrical wall;
   (b) an inflatable cuff on said main lumen between said proximal and distal ends;
   (c) a cuff-inflating lumen extending along said cylindrical wall between said cuff and the proximal end of said main lumen;
   (d) a suction chamber disposed on said main lumen adjacent the proximal side of said cuff, said chamber having a larger diameter than said main lumen and being in the shape of a bulge having a surface inclined at an acute angle to the vertical axis of said main lumen, said chamber containing a plurality of ports located on said inclined surface and spaced inwardly of the outer dimension of said chamber so that said ports do not contact the trachea when the endotracheal tube is inserted therein;
   (e) a chamber lumen extending along said wall between said chamber and the proximal end of said main lumen for suctioning out fluids in the trachea above said cuff and for introducing medicinal fluids into the trachea without causing trauma to the tracheal mucosa; and
   (f) means for applying suction to said chamber lumen.

2. An endotracheal tube as defined in claim 1 wherein the outer diameter of said suction chamber is approximately one-third greater than that of said main lumen.

3. An endotracheal tube as defined in claim 1 wherein said ports are ovoid in shape.

4. An endotracheal tube as defined in claim 3 wherein said chamber lumen is ovoid in cross-section.

5. An endotracheal tube as defined in claim 1 wherein said suction chamber contains four ports equally spaced around the inclined surface of said chamber.

6. An endotracheal tube as defined in claim 1 wherein said cuff-inflating and suction chamber lumens are located within the wall of said main lumen.

7. An endotracheal tube as defined in claim 1, further comprising means for applying a fluid jet stream to said suction lumen.

8. An endotracheal tube as defined in claim 1, wherein the diameter of said suction chamber is less than that of the inflated cuff, and wherein said ports are located immediately adjacent the wall of said main lumen.

* * * * *